(12) United States Patent
Gross et al.

(10) Patent No.: US 9,038,219 B2
(45) Date of Patent: May 26, 2015

(54) PATIENT SUPPORT APPARATUS AND ALSO A POSITIONING METHOD FOR POSITIONING A PATIENT'S HEAD WITHIN A SURGICAL HEAD RESTRAINT UNIT

(71) Applicants: Patrick Gross, Buckenhof (DE); Martin Ringholz, Erlangen (DE)

(72) Inventors: Patrick Gross, Buckenhof (DE); Martin Ringholz, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 0 days.

(21) Appl. No.: 13/952,867

(22) Filed: Jul. 29, 2013

(65) Prior Publication Data

US 2014/0033437 A1 Feb. 6, 2014

(30) Foreign Application Priority Data

Jul. 31, 2012 (DE) .......................... 10 2012 213 390

(51) Int. Cl.
| | | |
|---|---|---|
| *A47B 7/00* | (2006.01) | |
| *A61B 6/04* | (2006.01) | |
| *A61G 13/12* | (2006.01) | |
| *A61G 7/10* | (2006.01) | |
| *A61G 13/02* | (2006.01) | |

(52) U.S. Cl.
CPC ............ *A61B 6/0421* (2013.01); *A61G 13/121* (2013.01); *A61G 7/103* (2013.01); *A61G 7/1034* (2013.01); *A61G 13/02* (2013.01); *A61G 13/1295* (2013.01)

(58) Field of Classification Search
CPC .... A61B 5/0555; A61B 6/0442; A61B 5/055; A61B 6/0421; A61B 19/203; A61B 2019/5236; A61G 13/121; A61G 7/072; A61G 13/02; A61G 13/0036; A61G 13/101; A61N 5/1049; A61N 2005/1097
USPC ........................ 5/601, 622, 635, 637; 600/415
See application file for complete search history.

(56) References Cited

U.S. PATENT DOCUMENTS

| | | | | |
|---|---|---|---|---|
| 4,550,713 | A * | 11/1985 | Hyman ........................... 600/21 |
| 5,097,495 | A * | 3/1992 | Gray et al. ..................... 378/117 |
| 5,233,713 | A * | 8/1993 | Murphy et al. ................... 5/636 |
| 5,735,278 | A * | 4/1998 | Hoult et al. .................... 600/422 |
| 5,805,658 | A * | 9/1998 | Hum et al. ......................... 378/4 |
| 6,459,923 | B1 * | 10/2002 | Plewes et al. ................. 600/411 |
| 7,117,551 | B1 * | 10/2006 | Dinkler et al. .................... 5/637 |
| 7,446,304 | B2 * | 11/2008 | Li ............................. 250/227.14 |
| 7,857,512 | B2 * | 12/2010 | Camus ........................ 378/196 |
| 8,161,585 | B2 * | 4/2012 | Kuro et al. ......................... 5/601 |
| 2009/0056022 | A1 * | 3/2009 | Reitz et al. ......................... 5/601 |

(Continued)

OTHER PUBLICATIONS http ://www.noras.de/download/Datenblatt_OR_Kopfhalter.pdf, Mar. 2008.

(Continued)

*Primary Examiner* — Robert G Santos
*Assistant Examiner* — Richard G Davis

(57) ABSTRACT

A patient support apparatus having a support table, a transfer plate, which is disposed movably in relation to the support table in a direction and on which a patient is supported for a surgical intervention and/or a medical imaging examination, and a surgical head restraint unit, which is disposed on the transfer plate is provided. The patient support apparatus includes a position monitoring apparatus for monitoring and/or checking a position of the surgical head restraint unit.

12 Claims, 3 Drawing Sheets

(56) References Cited

U.S. PATENT DOCUMENTS

| | | | | |
|---|---|---|---|---|
| 2009/0056023 | A1* | 3/2009 | Calderon et al. | 5/601 |
| 2009/0260636 | A1* | 10/2009 | Markstroem | 128/869 |
| 2010/0205740 | A1* | 8/2010 | Tybinkowski et al. | 5/601 |
| 2010/0296723 | A1* | 11/2010 | Greer et al. | 382/153 |
| 2010/0329414 | A1* | 12/2010 | Zhu et al. | 378/4 |
| 2012/0124742 | A1* | 5/2012 | Soto et al. | 5/600 |

OTHER PUBLICATIONS http://www.gehealthcare.com/usen/mr/docs/Surg_Suite.pdf.
www.brainlab.com/art/2844/intra-operative-mri/, copyright 2012.
http:www.imris.com/product/neurosurgery, 2012.

* cited by examiner

PATIENT SUPPORT APPARATUS AND ALSO A POSITIONING METHOD FOR POSITIONING A PATIENT'S HEAD WITHIN A SURGICAL HEAD RESTRAINT UNIT

CROSS REFERENCE TO RELATED APPLICATIONS

The present application claims priority to European Patent Office application No. 10 2012 213390.9 DE filed Jul. 31, 2012, the entire content of which is hereby incorporated herein by reference.

FIELD OF INVENTION

The present invention relates to a patient support apparatus, comprising a support table, a transfer plate which is disposed to allow it to be moved in a direction relative to the support table and on which a patient is supported for a surgical intervention and/or a medical imaging examination, and a surgical head restraint unit which is disposed on the transfer plate.

BACKGROUND OF INVENTION

For neurosurgical interventions the patient is positioned on a patient support apparatus, especially an operating table apparatus. In this procedure the patient is positioned on a transfer plate, since frequently during an interruption to the neurosurgical intervention and/or after the ending of the neurosurgical intervention, a medical imaging examination, for example a magnetic resonance examination of the head region of the patient, is carried out. In such cases the patient is switched by means of the transfer plate between the operating table and a further patient support apparatus, which is especially embodied as magnetic resonance-compatible for a magnetic resonance examination. For the neurosurgical intervention a surgical head restraint unit is attached to the patient, especially to the patient's head, or the patient's head is positioned within this surgical head restraint unit, wherein the surgical head restraint unit is for example disposed on the transfer plate and projects, together with the patient's head, beyond the transfer plate.

A maximum permissible residence area or positioning area is available for the surgical head restraint unit, which is especially dimensioned in accordance with a cross-sectional surface of a patient receiving area of the medical imaging apparatus. If the surgical head restraint unit projects beyond the maximum allowable positioning area for the surgical head restraint unit this can lead, during an introduction of the patient positioned on the transfer plate together with the surgical head restraint unit into the patient receiving area, to undesired collisions, especially with a housing of the medical imaging apparatus. This increases the risk of injury for the patient. In addition the surgical head restraint unit must be repositioned to enable any medical imaging examination at all to be performed. This repositioning can lead to undesired delays, since a sterile cover of the surgical head restraint unit first has to be dismantled for the repositioning.

The positioning of the surgical head restraint unit and/or of the patient's head is carried out by a surgeon and/or clinical operating personnel, wherein this positioning is very complex. In addition this positioning is undertaken on the basis of a rough estimation of the maximum permissible positioning area and/or in accordance with empirical values of the surgeon and/or of the operator. This can lead however to only a fraction of the maximum permissible positioning area being used or can still lead to collisions during the insertion into the medical imaging apparatus for instance.

SUMMARY OF INVENTION

The particular object of the present invention is to provide a patient support apparatus in which a time-saving and simple fixing and/or positioning of the patient's head within the surgical head restraint unit can be achieved. The object is achieved by means of the features of the independent claims. Advantageous embodiments are described in the subclaims.

The invention is based on a patient support apparatus comprising a support table, a transfer plate which is disposed to enable it to be moved in a direction relative to the support table and on which a patient is supported for a surgical intervention and/or a medical imaging examination, and a surgical head restraint unit which is disposed on the transfer plate.

It is proposed that the patient support apparatus has a position monitoring apparatus for monitoring and/or checking a position of the surgical head restraint unit. This enables a simple and fast positioning and/or fixing of the head of the patient together with the surgical head restraint unit to be made possible on the movable support plate in an examination position and/or an operating position. In addition adhering to a maximum permissible residence area and/or positioning area for the surgical head restraint unit during a positioning of the surgical head restraint unit on the transfer plate and/or the support table during a positioning of the patient's head within the surgical head restraint unit can be achieved especially easily. Furthermore in this way the patient can be introduced safely into the medical imaging apparatus together with the surgical head restraint unit for a subsequent medical imaging examination, wherein a danger of infection and/or a danger of injury for the patient, such as for example during a collision of the surgical head restraint unit with a housing of the medical imaging apparatus, can be kept especially low. Furthermore a time-saving and/or money-saving preparation of the patient, especially positioning of the patient, can be advantageously achieved and during this process a workflow for the clinical operating personnel can be advantageously optimized.

Preferably the surgical head restraint unit comprises a surgical head securing unit in which the head of the patient is supported rigidly and immovably for the imminent surgical intervention, so that a movement of the head and/or an undesired change in position of the head during the surgical intervention and/or the medical imaging examination can be excluded. The surgical head restraint unit can additionally have a sterile cover which, after a positioning and/or fixing of the patient's head within the surgical head restraint unit, is disposed above the head area of the patient.

It is further proposed that the patient support apparatus has a maximum permissible positioning area for the surgical head restraint unit and the position monitoring apparatus is disposed at least partly at an edge area of the maximum permissible positioning area. In this connection a maximum permissible positioning area for the surgical head restraint unit is to be understood especially as an area of which the extent corresponds essentially to a maximum extent of an opening of a patient receiving area to receive the patient for a medical imaging examination of the medical imaging apparatus minus a safety area and/or a tolerance range. This embodiment enables adherence to the maximum permissible positioning area for the surgical head restraint unit during a positioning process of the surgical head restraint unit on the transfer plate to be monitored in an especially simple manner, especially since the position monitoring apparatus is already disposed in a critical positioning area. The maximum permissible positioning area is preferably disposed in a front area and/or a head support area of the patient support apparatus, since the surgical head restraint unit is also disposed in this front area and/or a head support area. Preferably the position monitoring apparatus is also disposed on the transfer plate and/or on the support table in this front area and/or head support area of the patient support apparatus, so that an advantageous position monitoring can also be achieved in a possible collision area and/or danger area.

An especially space-saving arrangement and a compact patient support apparatus can be advantageously achieved if the position monitoring apparatus is disposed on the support table and/or on the transfer plate. Especially advantageously the position monitoring apparatus is disposed on a side of the transfer plate facing towards the support table and/or on a side of the support table facing towards the transfer plate. This allows a support area of the patient support apparatus to be available without restriction for supporting the patient.

If the position monitoring apparatus is disposed on the transfer plate, it can be advantageous for the support table to have a cutout which is disposed on a side facing towards the transfer plate and which extends in a longitudinal direction of the support table. In this way, during a switch and/or transfer of the patient together with the transfer plate, a collision and/or an obstruction of the position monitoring apparatus with the support table can advantageously be prevented.

In an advantageous development of the invention it is proposed that the patient support apparatus has an attachment unit for removable attachment of the position monitoring apparatus on the support table and/or the transfer plate. In this case for example the position monitoring apparatus can especially advantageously be removed from the transfer plate during a transport of the transfer plate and/or the position monitoring apparatus can be disposed on or attached to the transfer plate and/or the support table only during the use of a patient support apparatus together with the surgical head restraint unit.

If the position monitoring apparatus includes an adjustment unit, the position monitoring apparatus can be adapted especially advantageously to different medical imaging apparatuses, especially to differently-embodied patient receiving areas for receiving the patients. In addition the patient monitoring apparatus can advantageously be adapted in this way, after its removal from the patient support apparatus and its rearrangement on the patient support apparatus, especially on the support table and/or the transfer plate, to the maximum permissible positioning area or the patient receiving area of the medical imaging apparatus.

An especially low-cost position monitoring apparatus can be achieved if the position monitoring apparatus features a mechanical target checking unit with an aiming unit. Preferably, by means of the mechanical target checking unit, especially the aiming unit, aiming at an endangered area of the maximum permissible positioning area for the surgical head restraint unit is possible so that a safe and simple positioning of the surgical head restraint unit on the transfer plate is made possible. Advantageously the aiming unit comprises at least two sighting elements for this purpose so that simple aiming is possible. The at least two aiming elements can for example be formed by a front and rear sight system. In addition further embodiments of the at least two aiming elements are also always conceivable by the person skilled in the art.

Furthermore it is proposed that the at least two aiming elements are disposed one after the other in a viewing direction and this viewing direction includes a target area of the aiming unit, wherein this target area coincides at least partly with an edge area and/or a delimitation of the maximum permissible positioning area for the surgical head restraint unit. A viewing direction should be understood in this context as especially a viewing direction of a clinical operator during an aiming of the two aiming elements, wherein the viewing direction comprises an imaginary connection between the at least two aiming elements and/or a direction along an optical axis between the at least two aiming elements. Through this embodiment of the invention a direct checking of the position of the surgical head restraint unit can be achieved by for example a clinical operator looking immediately after the positioning along the viewing direction through the position monitoring apparatus.

Preferably a mispositioning of the surgical head restraint unit is identified by an at least partial arrangement of the surgical head restraint unit and and/or at least partial arrangement of the patient's head within a target area of the aiming unit. In this way a mispositioning of the surgical head restraint unit and/or of the patient's head when the target area is aimed at by the aiming unit can be detected especially easily by a clinical operator. In addition a position correction of the surgical head restraint unit during a positioning process of the patient, especially of the patient's head within the surgical head restraint unit can be initiated directly by this method before the imminent surgical intervention.

The transfer plate, together with the surgical head restraint unit and the position monitoring apparatus, can be employed for positioning the patient in all medical imaging apparatuses known to the person skilled in the art. If the transfer plate together with the position monitoring apparatus is embodied to be compatible with magnetic resonance for example, the transfer plate can be used to particular advantage together with a magnetic resonance apparatus.

Furthermore the invention is also based on a medical imaging device with a patient support apparatus, as claimed in the claims. In this way the patient, together with the surgical head restraint unit, can be introduced safely into the medical imaging apparatus for a medical imaging examination. By adhering to the maximum positioning area during the positioning of the surgical head restraint unit, a danger of a collision between the surgical head restraint unit and a detector unit of the medical imaging apparatus and/or a housing surrounding the patient receiving area of the medical imaging apparatus can advantageously be minimized. In such cases a danger of infection and/or a danger of injury for the patient, such as for example during a collision between the surgical head restraint unit and a housing of the medical imaging apparatus, can be kept especially low.

The invention is also based on a positioning method for positioning a patient's head within a surgical head restraint unit, comprising the following method steps:

A positioning of the patient's head within the surgical head restraint unit,

A positioning of the surgical head restraint unit within a maximum permissible positioning area on a transfer plate and Checking the position of the surgical head restraint unit on the transfer plate by means of a position monitoring apparatus.

This especially advantageously enables a workflow for a clinical operator during a positioning of the patient's head within the surgical head restraint unit and/or a positioning of the surgical head restraint unit on the transfer plate to be optimized, in that by means of the position monitoring apparatus a positioning aid is available to the clinical operator during the positioning steps and thus mispositioning can be detected directly. In addition safety for the patient, especially during an interruption to the surgical intervention for a medical imaging examination, is advantageously enhanced by means of the inventive method. In this connection checking of the position of the surgical head restraint unit should be understood as being an optical check by means of the mechanical target checking unit, especially by means of the aiming unit by a clinical operator.

Furthermore it is proposed that in the method step of checking the position of the surgical head restraint unit, a mispositioning of the surgical head restraint unit is detected on the basis of an at least partial arrangement of the surgical head restraint unit in a target area of the position monitoring apparatus. In this way a mispositioning of the surgical head restraint unit can be detected especially easily by a clinical operator when the target area is being targeted by means of the aiming unit.

In an advantageous development of the inventive positioning method it is proposed that, if a mispositioning of the surgical head restraint unit is present, the head restraint unit is repositioned on the transfer plate. In this way the position of the surgical head restraint unit on the transfer plate and/or the position of the patient's head within the surgical head restraint unit can be corrected especially quickly during a positioning process of the patient before the imminent surgical intervention. Especially advantageously, after a repositioning of the surgical head restraint unit, the position of the surgical head restraint unit on the transfer plate is checked once again by means of the position monitoring device. Preferably the positioning method is not ended until the surgical head restraint unit is disposed completely within the maximum permissible positioning area. Only once this has been done can the surgical intervention on the patient be started.

BRIEF DESCRIPTION OF THE DRAWINGS

Further advantages, features and details of the invention will emerge from the exemplary embodiment described below and with the aid of the drawings.

In the figures.

DETAILED DESCRIPTION OF INVENTION

Figure 1:
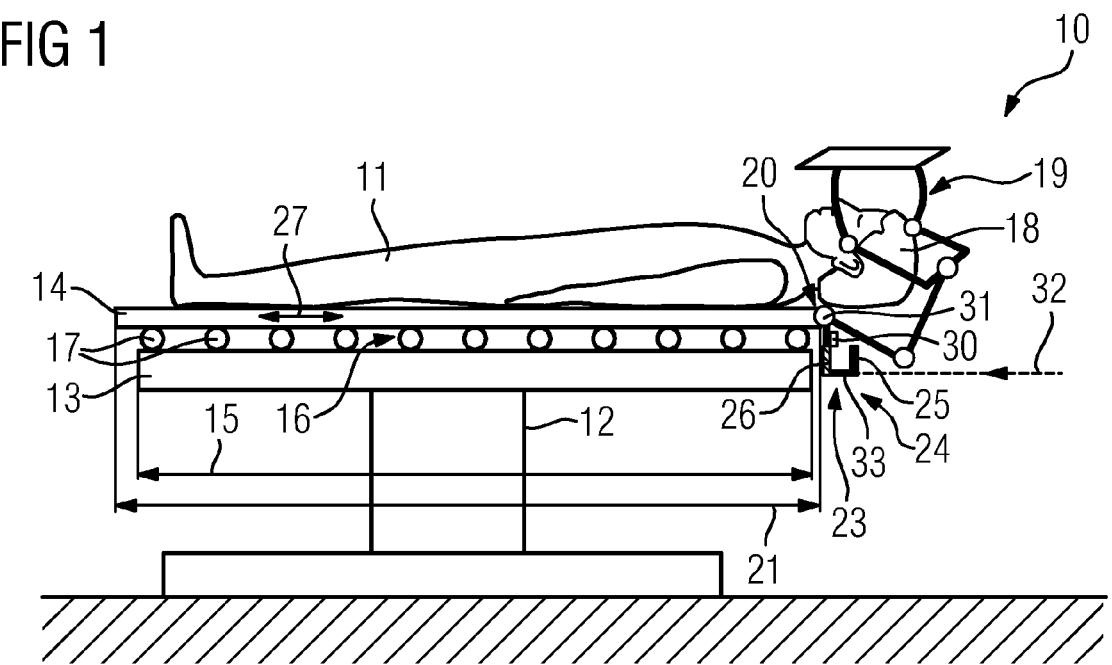
FIG. 1 shows a schematic side view of a patient support apparatus.
Figure 2:
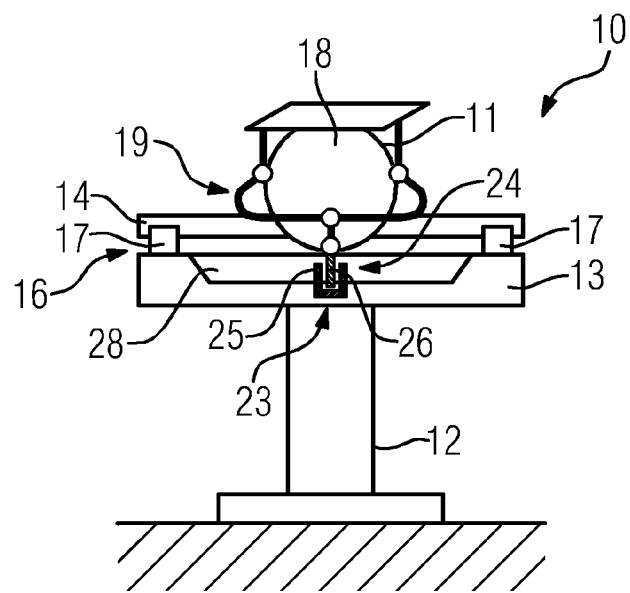
FIG. 2 shows a schematic front view of the patient support apparatus.

A schematic side view of an inventive patient support apparatus 10 is shown in FIG. 1 and FIG. 2. The patient support apparatus 10 is formed here by an operating table apparatus. However the patient support apparatus 10 can also be formed by a movable patient support apparatus 114, by means of which the patient 11 can be transported to a medical imaging apparatus and on which the patient 11 can be supported for a medical imaging examination, as is especially shown in FIG. 4.

The patient support apparatus 10 has a base unit 12, by means of which the patient support apparatus 10 is supported on a floor surface. Furthermore the patient support apparatus 10 has a support table 13 and a transfer plate 14. The support table 13 is disposed on a side of the base unit 12 facing away from a floor surface. On a side of the support table 13 facing away from the base unit 12 the transfer plate 14 is supported on the support table 13, wherein the transfer plate 14 is supported movably relative to the support table 13 along a longitudinal extent 21 of the transfer plate and/or along a longitudinal extent 15 of the support table 13. To this end the patient support apparatus 10 also has a sliding bearing unit 16 comprising individual sliding bearing elements 17 such as slide rollers for example, by means of which a low-friction movement or a low-friction sliding of the transfer plate 14 in relation to the support table 13 is made possible. The slide bearing unit 16 is disposed in this case between the support table 13 and the transfer plate 14.

Because of the movable support of the transfer plate 14 on the support table 13, the transfer plate 14 is able to be swapped between different patient support apparatuses 10. For example the patient 11 is positioned on the transfer plate 14, wherein the transfer plate 14 is latched, especially immovably, to the support table 13 for this purpose via a latching unit not shown in any greater detail. For the surgical intervention the patient 11 together with the transfer plate 14 remains on the operating table apparatus. If a medical imaging examination occurs after the end and/or during an interruption to the surgical intervention, the patient 11 lying on the transfer plate 14 will be switched from the operating table apparatus to a further patient support apparatus 10. This further patient support apparatus 10 couples to the medical imaging apparatus 100 so that the transfer plate 14 together with the patient 11 can be introduced into a patient receiving area 101.

For a neurosurgical intervention on the patient 11, the patient 11, especially the head 18 of the patient 11, is positioned within a surgical head restraint unit. The surgical head restraint unit comprises a surgical head securing unit 19 which is disposed in a front area 20 and/or head area of the transfer plate 13. The surgical head securing unit 19 projects beyond the front area 20 and/or head area of the transfer plate 14, so that the head 18 of the patient 11 also projects along the longitudinal extent 21 of the transfer plate 14 beyond said plate.

The surgical head securing unit 19, together with the head 18 of the patient 11, must be positioned in this case on the transfer plate 14 such that during a transfer of the transfer plate 14 and the patient 11, a collision between the surgical head securing unit 19 and the support table 13 and also a housing 102 surrounding the patient receiving area 101 of the medical imaging device 100 is prevented. For this purpose a maximum permissible positioning area 22 is available for the surgical head restraint unit 19. This maximum permissible positioning area 22 is defined on the basis of a cross-sectional surface 103 of the patient receiving area 101 minus a safety area and/or a tolerance area (see FIG. 4)

For adherence to and/or monitoring of a position of the surgical head securing unit 19 within the maximum permissible positioning area 22 during a positioning of the head 18 of the patient 11 within the surgical head securing unit 19 and of the surgical head securing unit 19 on the transfer plate 14, the patient support apparatus 10 additionally has a position monitoring apparatus 23 (FIGS. 1 and 2).

Figure 3:
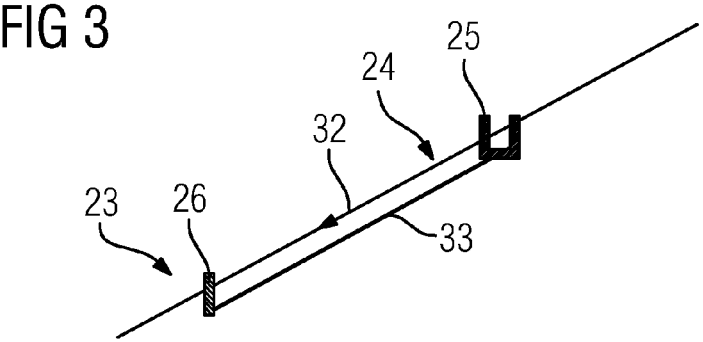
FIG. 3 shows a position monitoring apparatus in a detailed view.

The position monitoring apparatus 23 has a mechanical target checking unit with an aiming unit 24, which in the present exemplary embodiment comprises two aiming elements 25, 26, as is shown in greater detail in FIG. 3. A first of the two aiming elements 25 is formed by a front sight and a second of the two aiming elements 26 is formed by a rear sight of a front and rear sight system. In an alternative embodiment the aiming units 24 can also have more than two aiming elements 25, 26 or more than one front and rear sight system.

In the present exemplary embodiment the position monitoring apparatus 23 is disposed in the front area 20 and/or the head area of the transfer plate 14. Here the position monitoring apparatus 23 is also disposed on a side of the transfer plate 14 facing away from the support table 13, so that the patient 11 can lie comfortably without restrictions through the arrangement of the position monitoring apparatus 23 on the transfer plate 14. As an alternative to this, it is likewise conceivable in a further embodiment of the invention for the position monitoring apparatus 23 to be disposed in a front area and/or head area of the support table 13, especially on a side of the support table 13 facing towards the transfer plate 14.

The support table 13 has a cutout 28 and/or a recess along its longitudinal extent 15 and/or along a direction of movement 27 of the transfer plate 14 in relation to the support table 13 during a movement of the transfer plate 14 in relation to the support table 13, so that a collision between the position monitoring apparatus 23 and the support table 13 is prevented during a transfer of the transfer plate 14 together with the position monitoring apparatus 23. The cutout 28 is disposed on the side of the support table 13 facing towards the transfer plate 14 on said table, as is shown in greater detail in FIG. 2.

Figure 4:
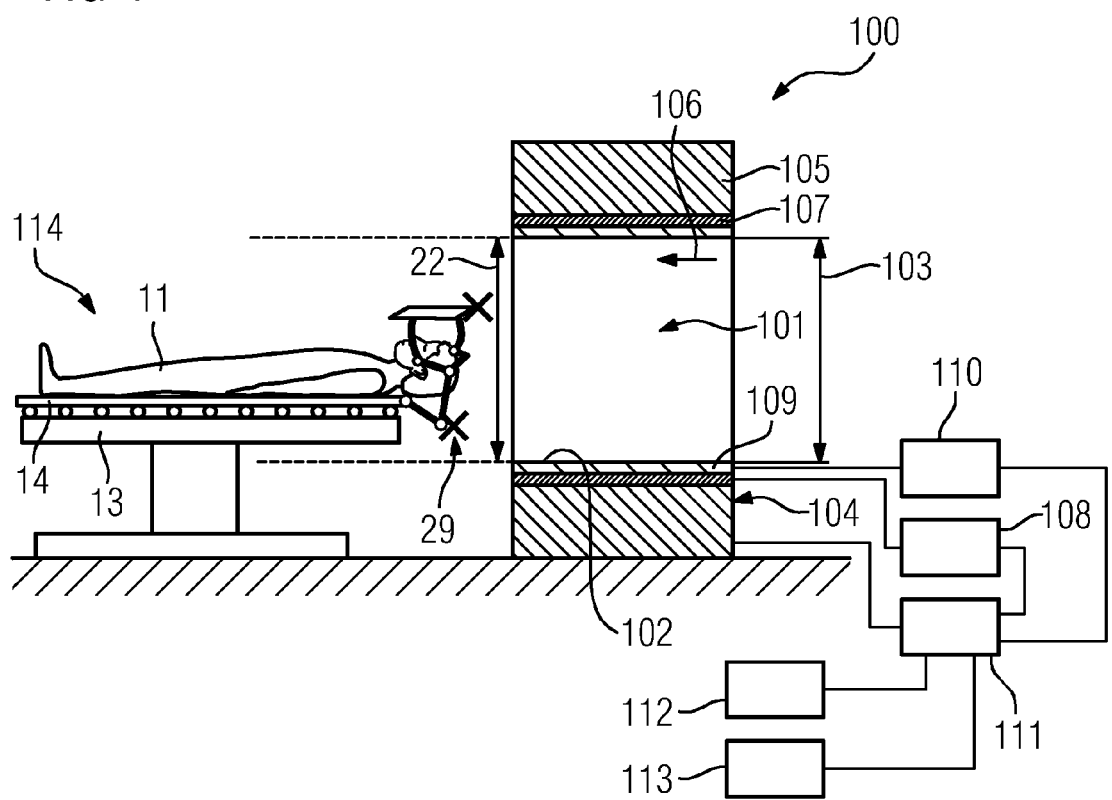
FIG. 4 shows a medical imaging apparatus with a patient support apparatus in a schematic diagram and FIG. 5 shows an inventive positioning method.

The position monitoring apparatus 23 is disposed within the front area 20 on the transfer plate 14 so that in particular the aiming unit 24 is disposed within an edge area and/or a critical collision area 29 of the maximum permissible position monitoring area 22 (FIG. 4). For setting an arrangement of the position monitoring apparatus 23, especially of the aiming unit 24 within the edge area of the maximum permissible position monitoring area 22, the position monitoring apparatus 23 has an adjustment unit.

Furthermore the patient support apparatus 23 comprises an attachment apparatus 31 for a removable attachment of the position monitoring apparatus 23 to the transfer plate 14.

The two aiming elements 25, 26 of the aiming unit 24 are disposed behind one another along a direction of view 32 of a clinical operator. To this end the aiming unit 24 has a spacing element 33, in the two end areas of which one of the two aiming elements 25, 26 is disposed in each case. A longitudinal extent of the distance element 33 in this case is aligned in parallel to a longitudinal extent 21 and/or a surface on which the transfer plate 14 lies.

The direction of view 32 extends from the aiming element 25 embodied as the front sight in the direction of the aiming element 26 embodied as the rear sight. The direction of view 32 in this case corresponds to a direction along an imaginary connection between the at least two aiming elements 25, 26 and/or a direction along an optical access between the at least two aiming elements 25, 26. The direction of view 32 includes a target area, which is defined by the two aiming elements 25, 26. This target area coincides with the edge area and/or a delimitation of the maximum permissible positioning area 22 for the surgical head securing unit 19. A mispositioning of the surgical head securing unit 19 is recognized and/or defined in this case by an at least partial arrangement of the surgical head securing unit 19 and/or an at least partial arrangement of the head 18 of the patient 11 within the target area of the aiming unit 24. Here the clinical operator looks along the direction of view 32 through the aiming units 24. If at least one of the two aiming elements 25, 26 is at least partly covered by the surgical head securing element 19 and/or the head 18 of the patient 11 and is thus not visible for the clinical operator along the direction of view 32, there is a mispositioning of the surgical head securing element 19. In this way an optical check for checking the positioning of the surgical head securing element 19 is carried out.

In FIG. 4 a medical imaging apparatus 100 formed by a magnetic resonance apparatus is shown schematically. The embodiment of the medical imaging apparatus 100 is however not restricted to the present exemplary embodiment. As an alternative or in addition the medical imaging apparatus 100 can also be formed by a computed tomography apparatus and/or a PET (positron emission tomography) apparatus etc.

The magnetic resonance device comprises a detector unit 104 formed by a magnet unit and having a main magnet 105 for generating a strong and especially constant main magnetic field 106. The magnetic resonance device also has the cylinder-shaped patient receiving area 101 for receiving the patient 11 for the magnetic resonance examination, wherein the patient receiving area 101 is enclosed by the detector unit 104 in the form of a cylinder in a circumferential direction. The patient 11 can be pushed by means of the patient support apparatus 114 into the patient receiving area 101.

The patient support apparatus 114 is formed by a moveable patient support apparatus 114 for transporting the patient 11 to the magnetic resonance apparatus. The support table 13 and the transfer plate 14 of the patient support apparatus 114 are embodied in a similar way to that described for FIGS. 1 to 3. In addition the transfer plate 14 and the position monitoring device 23 are embodied to be compatible with magnetic resonance.

The magnet unit additionally has a gradient coil unit 117 for generating magnetic field gradients, which is used for spatial encoding during an imaging session. The gradient coil unit 107 is controlled by means of a gradient coil control unit 108. The magnet unit also has a radio frequency antenna unit 109 and a radio frequency antenna control unit 110 for stimulating a polarization which develops in the main magnetic field 106 generated by the main magnet 105. The radio frequency antenna unit 109 is controlled by the radio frequency antenna control unit 110 and emits radio frequency magnetic resonance sequences into the patient receiving area 101.

For control of the main magnet 105, the gradient coil control unit 108 and for control of the radio frequency antenna control unit 110, the magnetic resonance apparatus has a control unit 111 formed by a processing unit. The control unit 111 controls the magnetic resonance apparatus centrally, such as the execution of a predetermined imaging gradient echo sequence for example. Control information such as imaging parameters for example, as well as reconstructed magnetic resonance images, can be displayed on a display unit 112, for example on at least one monitor of the magnetic resonance apparatus for an operator. In addition the magnetic resonance apparatus has an input unit 113, by means of which the information and/or parameters can be entered during a measurement process by an operator.

Figure 5:
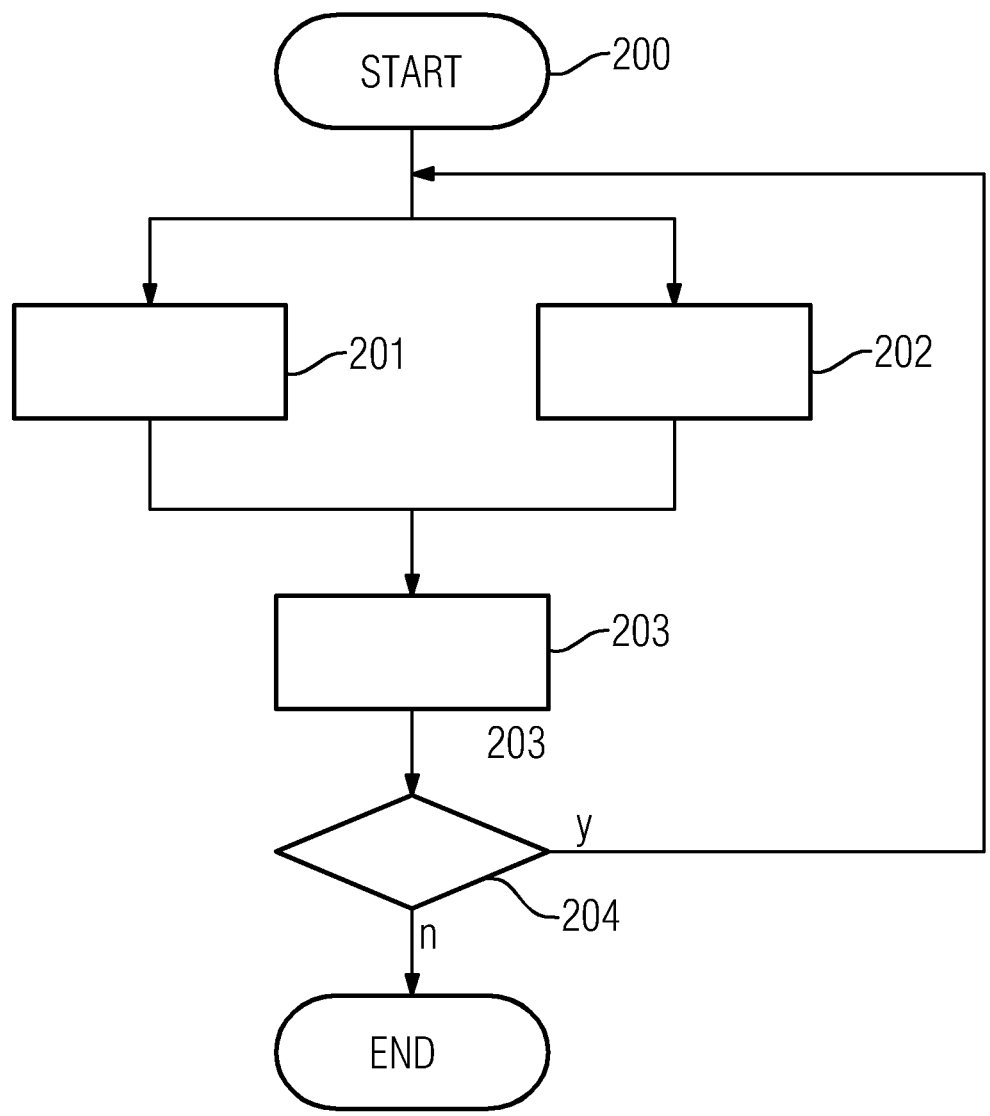

FIG. 5 shows a schematic diagram of an inventive positioning method for positioning the head 18 of the patient 11 within the surgical head securing unit 19. After a start 200 of the positioning method, in a first method step 201 the head 18 of the patient 11 is positioned within the surgical head restraint unit 19. At the same time, in a second method step 202 the surgical head restraint unit 19 on the transfer plate 14 is positioned within the maximum permissible positioning area 22 for the surgical head securing unit 19. In order to avoid a mispositioning of the surgical head securing unit 19, for example because the surgical head securing unit 19 is projecting beyond the maximum permissible positioning area 22, in a further method step 203 the position of the surgical head securing unit 19 on the transfer plate 14 is checked by means of the position monitoring apparatus 23.

In the method step 203 of checking the position of the surgical head securing unit 19, a mispositioning 204 of the surgical head securing unit 19 is recognized on the basis of an at least partial arrangement of the surgical head restraint unit 19 in the target area of the position monitoring apparatus 23, especially aiming unit 24, by during an optical check and/or looking through the aiming unit 24 in the direction of view 32 at least one of the two aiming elements 25, 26 being covered by the surgical head securing unit 19 and/or the head 18 of the patient 11.

If there is a mispositioning 204 of the surgical head securing unit 19, the clinical operator repositions the surgical head securing unit 19 on the transfer plate 14. At the same time the head 18 can also be repositioned within the surgical head securing unit 19. Subsequently the method step 203 of checking the position of the surgical head securing unit is executed again, so that this repositioning can subsequently be checked by the clinical operator.

Only when the surgical head securing unit 19 is correctly positioned within the maximum permissible positioning range for the surgical head securing unit 19 is an abort criterion fulfilled for ending the method.

We claim:

1. A patient support apparatus, comprising:
   a support table;
   a transfer plate, which is disposed to enable it to move in a direction relative to the support table and on which a patient is supported for a surgical intervention and/or a medical imaging examination;
   a surgical head restraint unit which is disposed on the transfer plate; and
   a position monitoring apparatus for monitoring and/or checking a position of the surgical head restraint unit,
   wherein the position monitoring apparatus includes a mechanical target checking unit with an aiming unit,
   wherein the aiming unit includes at least two aiming elements,
   wherein the at least two aiming units are disposed behind one another in a direction of view and the direction of view includes a target area of the aiming unit,
   wherein the target area coincides at least partly with an edge area and/or a delimitation of the maximum permissible positioning area for the surgical head restraint unit, and
   wherein a mispositioning of the surgical head restraint unit is determined if at least one of the at least two aiming units is not visible for a clinical operator along the direction of view.

2. The patient support apparatus as claimed in claim 1, wherein the surgical head restraint unit includes a maximum permissible positioning area, and wherein the position monitoring apparatus is disposed at least partly in an edge area of the maximum permissible positioning area.

3. The patient support apparatus as claimed in claim 1, wherein the position monitoring apparatus is disposed on the support table and/or the transfer plate.

4. The patient support apparatus as claimed in claim 1, wherein the position monitoring apparatus is disposed on a side of the transfer plate facing towards the support table or on a side of the support table facing towards the transfer plate.

5. The patient support apparatus as claimed in claim 1, wherein the position monitoring apparatus is disposed on a side of the transfer plate facing towards the support table and on a side of the support table facing towards the transfer plate.

6. The patient support apparatus as claimed in claim 1, wherein the support table includes a cutout, which is disposed on a side facing towards the transfer plate and which extends along a longitudinal extent of the support table, on the support table.

7. The patient support apparatus as claimed in claim 1, further comprising an attachment unit for removable attachment of the position monitoring apparatus to the support table and/or the transfer plate.

8. The patient support apparatus as claimed in claim 1, wherein the position monitoring apparatus is designed to be magnetic resonance-compatible.

9. A medical imaging apparatus, comprising:
   a patient support apparatus comprising:
      a support table;
      a transfer plate, which is disposed to enable it to move in a direction relative to the support table and on which a patient is supported for a surgical intervention and/or a medical imaging examination;
      a surgical head restraint unit which is disposed on the transfer plate; and
      a position monitoring apparatus for monitoring and/or checking a position of the surgical head restraint unit,
   wherein the position monitoring apparatus includes a mechanical target checking unit with an aiming unit,
   wherein the aiming unit includes at least two aiming elements,
   wherein the at least two aiming units are disposed behind one another in a direction of view and the direction of view includes a target area of the aiming unit,
   wherein the target area coincides at least partly with an edge area and/or a delimitation of the maximum permissible positioning area for the surgical head restraint unit, and
   wherein a mispositioning of the surgical head restraint unit is determined if at least one of the at least two aiming units is not visible for a clinical operator along the direction of view.

10. A positioning method for positioning a head of a patient within a surgical head restraint unit, comprising:
    positioning the head of the patient within the surgical head restraint unit;
    positioning of the surgical head restraint unit within a maximum permissible positioning area on a transfer plate; and
    checking the position of the surgical head restraint unit on the transfer plate by means of a position monitoring apparatus,
    wherein the position monitoring apparatus includes a mechanical target checking unit with an aiming unit,
    wherein the aiming unit includes at least two aiming elements,
    wherein the at least two aiming units are disposed behind one another in a direction of view and the direction of view includes a target area of the aiming unit,
    wherein the target area coincides at least partly with an edge area and/or a delimitation of the maximum permissible positioning area for the surgical head restraint unit, and
    wherein, in the checking the position of the surgical head restraint unit, a mispositioning of the surgical head restraint unit is detected if at least one of the at least two aiming units is not visible for a clinical operator along the direction of view.

11. The positioning method as claimed in claim 10, wherein when there is a mispositioning of the surgical head restraint unit the head restraint unit is repositioned on the transfer plate.

12. The positioning method as claimed in claim 10, wherein after a repositioning of the surgical head restraint unit, the position of the surgical head restraint unit on the transfer plate is checked again by means of the position monitoring apparatus.

* * * * *